(12) United States Patent
Hommann et al.

(10) Patent No.: US 7,815,598 B2
(45) Date of Patent: Oct. 19, 2010

(54) AUTO-PEN FOR A TWO-CHAMBER AMPOULE

(75) Inventors: Edgar Hommann, Grossaffoltern (CH); Benjamin Scherer, Uster (CH); Ian Thompson, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 982 days.

(21) Appl. No.: 11/218,322

(22) Filed: Sep. 1, 2005

(65) Prior Publication Data

US 2006/0111666 A1 May 25, 2006

(30) Foreign Application Priority Data

Sep. 2, 2004 (DE) .................. 10 2004 042 581

(51) Int. Cl.
*A61M 37/00* (2006.01)
(52) U.S. Cl. .................. 604/89; 604/191; 604/82; 604/92
(58) Field of Classification Search .......... 604/191, 604/155, 82, 218, 224, 208, 207, 211, 187, 604/181, 89, 90, 91, 92, 220, 246, 83, 84, 604/85, 86, 87, 88, 93.01
See application file for complete search history.

(56) References Cited

U.S. PATENT DOCUMENTS

| | | | | |
|---|---|---|---|---|
| 2,459,875 A | * | 1/1949 | Folkman | 604/135 |
| 4,689,042 A | * | 8/1987 | Sarnoff et al. | 604/89 |
| 4,822,340 A | * | 4/1989 | Kamstra | 604/135 |
| 5,092,842 A | * | 3/1992 | Bechtold et al. | 604/135 |
| 5,665,071 A | * | 9/1997 | Wyrick | 604/134 |
| 5,743,889 A | * | 4/1998 | Sams | 604/211 |
| 5,769,824 A | * | 6/1998 | Hjertman et al. | 604/143 |
| 5,823,998 A | * | 10/1998 | Yamagata | 604/131 |
| 5,925,019 A | * | 7/1999 | Ljungquist | 604/191 |
| 5,984,897 A | * | 11/1999 | Petersen et al. | 604/187 |
| 6,004,298 A | * | 12/1999 | Levander | 604/211 |
| 6,387,074 B1 | * | 5/2002 | Horppu et al. | 604/89 |
| 6,387,078 B1 | * | 5/2002 | Gillespie, III | 604/181 |
| 6,899,698 B2 | * | 5/2005 | Sams | 604/211 |
| 7,407,494 B2 | * | 8/2008 | Bostrom et al. | 604/207 |
| 2002/0095120 A1 | * | 7/2002 | Larsen et al. | 604/187 |
| 2004/0049161 A1 | * | 3/2004 | Shearn | 604/224 |
| 2005/0049550 A1 | * | 3/2005 | Kirchhofer et al. | 604/82 |

FOREIGN PATENT DOCUMENTS

| | | |
|---|---|---|
| DE | 38 40 000 C1 | 7/1989 |
| DE | 102 15 297 A1 | 10/2003 |
| EP | 0 298 067 B1 | 1/1989 |
| EP | 0 328 699 B1 | 9/1991 |
| EP | 0 834 330 A3 | 4/1998 |

* cited by examiner

*Primary Examiner*—Kevin C Sirmons
*Assistant Examiner*—Shefali D Patel
(74) *Attorney, Agent, or Firm*—Dorsey & Whitney LLP; David E. Bruhn, Esq.

(57) ABSTRACT

An injection device for use with a two-chamber ampoule, wherein the device includes a front casing part with which the two-chamber ampoule can be associated, a rear casing part, a threaded drive accommodated by the rear casing part, a piston rod which, during a blending movement, is moved by the threaded drive toward a dispensing end of the device and slaves at least a closing piston of the two-chamber ampoule in the process, wherein a spring element presses the piston rod toward the dispensing end during a delivery movement.

25 Claims, 3 Drawing Sheets

AUTO-PEN FOR A TWO-CHAMBER AMPOULE

CROSS-REFERENCE TO RELATED APPLICATION

This application claims priority to German Application No. DE 10 2004 042 581.7, filed on Sep. 2, 2004, the contents of which is incorporated in its entirety herein by reference.

BACKGROUND

The invention relates to devices and methods for administering, delivering, dispensing or injecting substances. More particularly, it relates to a device and method for blending and administering substances or medicines which are not blended until immediately or very shortly prior to being administered. In one embodiment, the invention relates to a blending and administering device which is suitable for administering an injectable product from a two-chamber ampoule.

In various medical or therapeutic procedures, fluid products consisting of multiple components not blended until shortly prior to being administered, for example, growth hormones, need to be administered to a patient. One way of blending and administering such substances is to use a multi-chamber ampoule. In particular, two-chamber ampoules in which, for example, a fluid is provided as a solvent in a first chamber and a product component is provided in solid and/or fluid form in a second chamber, may be used. The solvent and the product component are blended in the ampoule by means of a blending device. With the aid of the blending device, the fluid product to be injected can be blended, shortly prior to being administered by an administering device, by shifting a plug within the multi-chamber ampoule in such a way that the solvent comes into contact with the product component via a supply channel and mixes with it.

When blending the fluid product, care should be taken that the mixing process is not carried out too quickly. Blending too quickly can lead to foam being undesirably formed in the fluid product. Furthermore, when blended quickly, it is possible for a solid product to not yet be completely dissolved in a solution by the time it is administered, or for a solution of the fluid product to not yet be homogenous.

In a conventional administering device, the multi-chamber ampoule is inserted into a casing of the device. The administering device comprises a blending device in which a drive means can be screwed into the casing with the aid of a thread. The drive means is manually screwed into the casing by a rotating movement in which it moves relative to and into the casing. By rotating the drive means of the blending device in, the plug is slowly moved axially along the ampoule within the multi-chamber ampoule. The rotating movement of the drive means is thus converted into a slow translational movement of the plug within the ampoule, such that a smooth blending is possible within the ampoule.

EP 0 328 699 B1 shows a syringe comprising a blending device, wherein the mixed product is injected into the patient after blending by the administering person pressing a piston rod.

EP 0 298 067 B1 discloses a device for producing an injection solution and for subsequently injecting this solution. Once the mixed product has been blended by the blending device, a product dose to be administered is administered in a controlled way by administering certain doses of the injection solution via a dosing means connected to the holding means of the container.

SUMMARY

It is an object of the invention to provide a device for blending and/or injecting a fluid product of a two-chamber ampoule, which enables the fluid product to be reliably blended and comfortably injected. This object is addressed by providing an injection device for use with a two-chamber ampoule.

In one embodiment, the invention relates to an injection device for use with a two-chamber ampoule, comprising a front casing part in which the two-chamber ampoule is contained or can be accommodated, a rear casing part, a threaded drive accommodated by the rear casing part, a piston rod which during a blending movement is moved by the threaded drive toward the end of the injection device at which the substance is dispensed, and slaves at least one main piston of the two-chamber ampoule in the process, wherein during a delivery movement, a spring element presses the piston rod toward the end of the injection device at which the substance is dispensed, i.e., away from the rear casing part.

The casing of the injection device consists of a front casing part and the rear casing part, which are preferably detachably connected to each other. The front casing part serves to accommodate the two-chamber ampoule. The ampoule can be either inserted into the front casing part or can form the front casing part. Similarly, the injection device can also be formed integrally as a disposable part.

The two-chamber ampoule can be inserted via a lateral opening associated with the front casing part. It is also possible to insert the ampoule via the distal end or via the proximal end of the front casing part. It should be noted that a two-chamber ampoule then comprises a bypass on its wall, such that a recess for the bypass is included in the front casing part as appropriate and enables the ampoule to be introduced along with the bypass into the front casing part. The front casing part and the rear casing part can also be integral, in which case the ampoule can for example be inserted via the side or the distal end of the casing and/or the front casing part.

The front casing part or section also includes means for affixing a cannula, a needle or a connection means for an injection system.

A threaded drive is located in the rear casing part. The threaded drive comprises a threaded rod comprising an outer thread and a threaded nut including an inner thread which co-operates with the outer thread of the threaded rod. The threaded rod is non-rotationally connected to a rotating knob. The threaded rod and the rotating knob can also be formed integrally. The threaded rod and the rotating knob are preferably connected to each other in a positive lock, providing the rotational block. When the two-chamber ampoule is blended, a rotating movement is transferred onto the threaded rod by rotating the rotating knob. The threaded rod carries out a rotating movement relative to the threaded nut, whereby via its thread pitch, the threaded nut carries out an axial movement relative to the threaded rod. Using the value of the thread pitch, it is thus possible to set the axial path of the threaded nut per rotation of the threaded rod or rotating knob. The threaded rod also exhibits an adjusting length which can be used for the threaded nut and which at least corresponds to the path which is required for blending the products contained in the ampoule.

A rotating knob is connected to the rear casing part such that it can be rotated relative to the rear casing part but cannot be shifted axially relative to the rear casing part. Consequently, the threaded rod also cannot be shifted axially relative to the rear casing part. The rotating knob may comprise at least one locking element which engages with a corresponding counterpart attached to the rear casing part. In some embodiments, this can be a locking stud which is formed on the rotating knob and grips behind a collar-shaped formation on the rear casing part. The rotating knob also comprises a marking on its proximal end which, in a blending process, allows the angular positions of the rotating knob to be checked.

A retainer is also located in the rear casing part and is non-rotational with respect to the rear casing part but can be axially shifted relative to the rear casing part. This can be achieved by providing a groove running or extending in the axial direction, with which a cam or similar means engages in order to block rotation. In one preferred embodiment, the groove may be formed in the rear casing part; the cam formed on the retainer. The groove can, however, also be formed by the retainer and the cam by the rear casing part. The retainer is connected to the threaded drive. This connection is preferably non-rotational. The retainer and the threaded nut do not carry out any movements relative to each other. The rotational block between the retainer and the threaded nut is ensured by connecting at least one of the two components non-rotationally to the rear casing part. The retainer is preferably formed such that it can at least partially surround the threaded rod. The retainer contains at least one recess which encloses at least one holding means, such that it is mounted in such a way that it can be shifted radially. The holding means can be a sliding block. In one preferred embodiment, the holding means is preferably a sphere. The rear casing part forms a guide for the retainer.

On at least a part of its length, the retainer forms a guide for the piston rod, enabling an axial movement of the piston rod relative to the retainer. The piston rod also comprises an axial stopper which can co-operate with a radial heel of the retainer and thus restricts the axial movement of the piston rod during the blending process. This stopper can be formed by a collar at the proximal end of the piston rod, which co-operates with the radial heel of the retainer. The radial heel of the retainer simultaneously forms the guide for the piston rod. A second guide for the piston rod can also be formed by the radial collar which is guided on its peripheral side by the inner wall of the retainer. The distance between the stopper surfaces of the radial heel and the radial collar at least corresponds to the path traveled by the piston in the two-chamber ampoule during the delivery movement.

The at least one recess serving as a guide for the at least one holding means is located in the retainer, preferably in the area of the radial heel. At least one hollow, with which the holding means can engage, is arranged in the piston rod. The at least one hollow is in particular positioned in the piston rod such that the holding means engages with it when the piston rod is biased or urged (i.e., when a force is being applied to it or on it). This at least one hollow is preferably a radial groove in the piston rod. The contour of the groove can exhibit a rounded shape. When using a sphere as a holding means, the groove can exhibit a depth corresponding at most to the radius of the sphere, such that when an axial force is exerted on the piston rod, at least a force component acts radially outwards on the at least one sphere. This can also be achieved if the groove exhibits a width which is smaller than the diameter of the sphere.

When the piston rod is biased, at least one holding means is radially inserted into the at least one hollow. Since, if an axial force is exerted on the piston rod, the holding means would be pressed out of the groove, the inner wall of the rear casing part serves as a stopper for the holding means, such that the holding means cannot move radially outwards, out of the inserted position. The radial thickness of the radial heel of the retainer corresponds approximately to the extent to which the holding means, when inserted, protrudes beyond the peripheral surface of the piston rod. The radial thickness of the radial collar of the retainer should at least be smaller than the diameter of the sphere. The at least one guide, contained in the retainer, for the at least one holding means should approximately correspond to the cross-section of the holding means. In the case of a sphere, this would be a bore running transversely to the longitudinal axis.

A facing surface is located at the distal end of the piston rod and co-operates with the facing surface of the closing piston of the two-chamber ampoule. In one embodiment of the invention, the piston rod and the closing piston could be fixedly connected to each other and/or formed integrally.

An elastic element, in particular a coil spring, is located between the threaded drive and the proximal end of the piston rod. The coil spring is at least partially enclosed on the peripheral side by the retainer. At least a part of the threaded rod can be located within the coil spring. When the piston rod is in its biased position, i.e., in the position in which the at least one holding means engages with the groove of the piston rod, the coil spring is compressed and biased (or tensed). The at least one holding means prevents the spring from being relaxed and the piston rod from consequentially moving towards the distal end of the injection device. A force component acting radially away from the longitudinal axis does act on the holding means, but the holding means is prevented from being ejected by the inner side of the rear casing part.

The flow of force generated by the coil spring runs from the spring into the threaded nut, via the retainer, the at least one holding means and the piston rod back into the spring, such that while the holding means is inserted, there is no degree of freedom allowing the piston rod to move in the distal direction (toward the needle end or, in other words, the end at which a substance is emitted or dispensed). The axial position of the at least one holding means relative to the threaded nut of the threaded drive is kept constant by the retainer.

The rear casing part is at least partially enclosed by a triggering sleeve, which is mounted by the rear casing part and can carry out a movement relative to the rear casing part. At least one blocking element is located on the triggering sleeve. The least one blocking element protrudes respectively through a window into the rear casing part. The number of blocking elements and the number of windows preferably corresponds to the number of holding means. The surface of the at least one blocking element facing in the longitudinal axis forms a radial stopper for at least one holding element, wherein the stopper preferably exhibits approximately the same radial distance from the longitudinal axis as the inner wall of the rear casing part. The triggering sleeve is pressed into a starting position by a spring element. The spring element can be supported on the front casing part and on the triggering sleeve. The spring is preferably biased, in order to exert a force on the triggering sleeve which presses the sleeve into the starting position.

The at least one window is preferably located in the rear casing part of the injection device. The window exhibits a width such that the blocking element can protrude through the window. The window also exhibits an axial length which is larger than the axial length of the blocking element, such that in one embodiment, the triggering sleeve can be axially slid back and forth. The axial length of the window should at least correspond to the sum of the axial length of the blocking element and the axial length of the holding means. When using a sphere as a holding means, the minimum length of the window is the sum of the axial length of the blocking element and the diameter of the circular cross-section which the sphere exhibits at the latitude, inserted into the window, at which the sphere releases the piston rod for an axial movement.

In another embodiment, the at least one window also exhibits a length and width such that the at least one blocking element can protrude through it, wherein the longer side of the window runs in the peripheral direction. The side of the window running in the peripheral direction is at least large enough for the at least one blocking element to be able to carry out a rotating movement with the protective sleeve, so that it releases the at least one holding means.

During the blending movement, the piston rod is moved towards the distal end of the injection device by rotating the rotating knob. The rotating movement of the rotating knob is transferred onto the threaded rod which moves relative to the threaded nut. Since the threaded nut carries out a rotational movement relative to the threaded rod, it is also moved via the thread pitch towards the proximal end of the injection device. This blending movement is transferred from the threaded drive onto the piston rod via the retainer, wherein the at least one holding means engages with the at least one hollow in the piston rod, such that during the blending movement, the holding means and/or retainer are fixed relative to the piston rod. The piston rod, the retainer, the at least one holding means, the threaded nut and the elastic element or coil spring are thus moved as a unit in the distal direction of the injection device during the blending movement. During the blending movement, the at least one holding means is held in the hollow by the rear casing part and thus moved relatively along the rear casing part.

When the piston rod is moved, at least the closing piston of the two-chamber ampoule is slaved. During the blending movement, the closing piston is moved towards the distal end of the two-chamber ampoule. Due to the incompressibility of the fluid product element between the closing piston and the dividing piston of the two-chamber ampoule, the dividing piston is likewise moved in the distal direction until the dividing piston has completely entered the area of the bypass. The dividing piston then no longer forms a seal, such that the fluid product can flow via the bypass into the chamber formed by the dividing piston and the closure of the two-chamber ampoule, and is mixed in said chamber with another product element and forms a mixed product. The blending process is complete when the two mutually facing surfaces of the closing piston and dividing piston contact. At this stage, the piston rod, the retainer, the coil spring and the at least one holding element have moved far enough in the distal direction for each holding means to be axially located in the area of the stopper surface of the blocking element of the triggering sleeve. A stopper is preferably formed in order to ensure the axial position of the holding elements. The stopper can for example be provided by an element which sits on the outer thread of the threaded rod and prevents the threaded nut from rotating further when the at least one holding element has reached its axial position level with the blocking means. A stopper can also be formed by the facing side of the retainer facing in the distal direction, said stopper abutting a surface of the front casing part when the holding elements are in a corresponding position. The at least one holding element is pressed into the hollow or groove in the piston rod by a blocking element at a first end position of the piston rod which is reached at the end of the blending movement.

The injection device is then ready to administer the mixed product. The blocking element releases the at least one holding element via a translational or rotational movement, such that the holding element is pressed approximately radially outwards due to the radial force component acting on it. The rotational, preferably translational movement of the holding element is caused by the movement of the triggering sleeve. The holding element is pressed radially outwards by the axial force of the biased coil spring on the piston rod, since the surface of the respective blocking element forming the radial stopper is no longer holding the at least one holding element back. In another embodiment, at least one blocking element releases at least one holding element by a translational or a rotational movement, such that each of them is pressed approximately radially outwards due to a force acting on the at least one holding element. In order to prevent the at least one holding element from falling out of the injection device, a part of the triggering sleeve is slid over the window. The at least one holding element is thus pressed into the window of the rear casing part, against the triggering sleeve slid over it. The spring element is preferably biased (or tensed) and the piston rod is released when the at least one holding means is released.

During the delivery movement, the piston rod carries out an axial movement in the distal direction relative to the threaded nut and/or retainer. In this way, the two pistons of the two-chamber ampoule are pressed in the distal direction via the piston rod by the force of the coil spring and thus deliver the mixed product from the two-chamber ampoule. The delivery process is complete when the facing surface of the dividing piston facing in the distal direction abuts the facing side of the two-chamber ampoule. The delivery process can also be complete when the radial collar of the piston rod abuts the radial heel of the retainer.

If a new two-chamber ampoule can be inserted into the injection device, the piston rod must be moved to its original position relative to the retainer. To this end, the piston rod is slid back by a force acting in the proximal direction, and the coil spring is thus biased. When the piston rod is slid back, the at least one hollow contained in it is axially moved into the area of the at least one holding element. A force comprising at least one force component facing radially to the longitudinal axis is transferred onto the at least one holding element by the spring element acting on the triggering sleeve. When the at least one hollow is located in the area of the at least one holding element, then the at least one holding element is pressed back into the at least one hollow by this force. The blocking element and the triggering sleeve connected to it snap back in the proximal direction relative to the rear casing part. The retainer and piston rod are fixed with respect to each other by the at least one holding element engaging with the piston rod. By rotating the rotating knob, the piston rod is moved back in the proximal direction together with the retainer, the at least one holding element, the threaded nut and the coil spring. Once a new two-chamber ampoule has been inserted, the device is ready for a new blending and/or a new injection or delivery.

DETAILED DESCRIPTION

Figure 1:
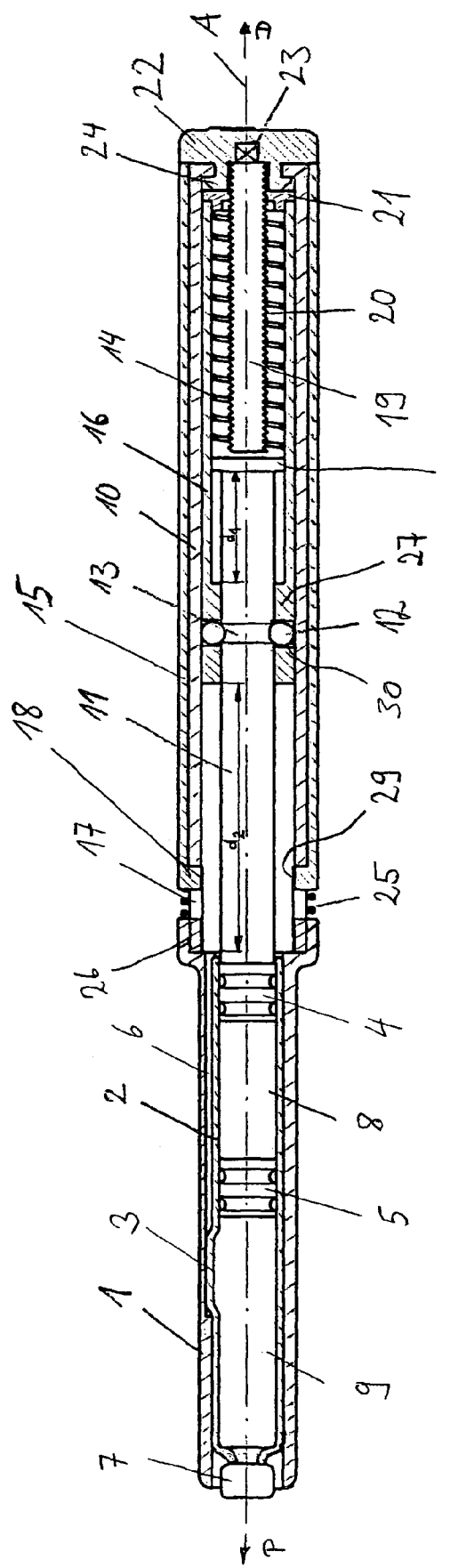
FIG. 1 is a sectional representation of one embodiment of an injection device in accordance with one embodiment of the present invention, in a starting state.
Figure 2:
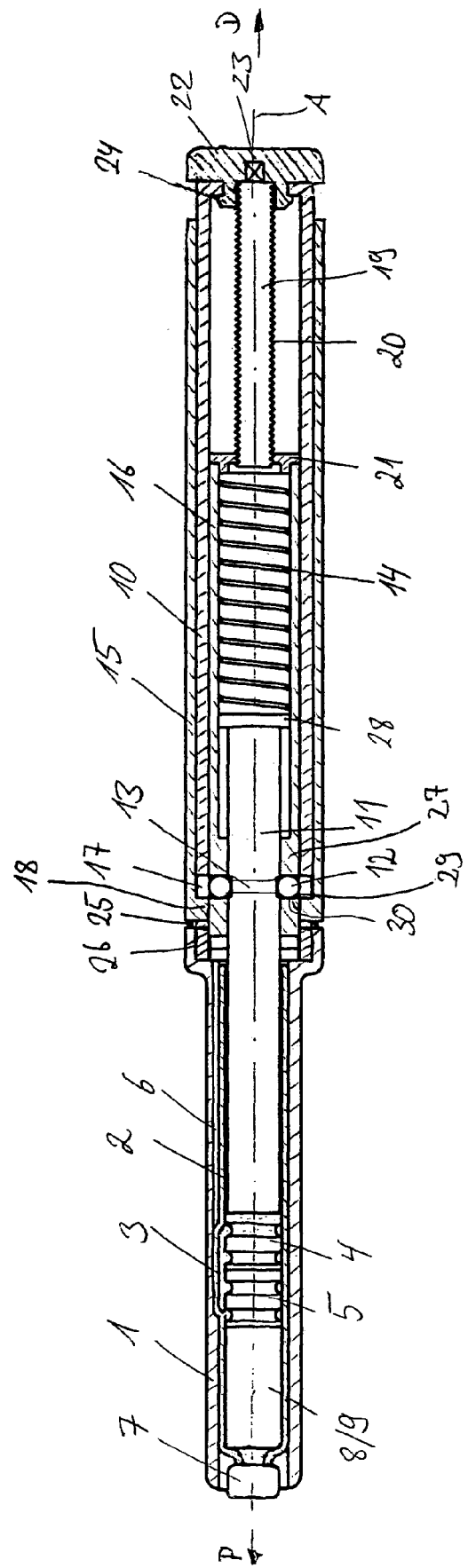
FIG. 2 is a sectional representation of the injection device from FIG. 1, at the end of the blending process.
Figure 3:
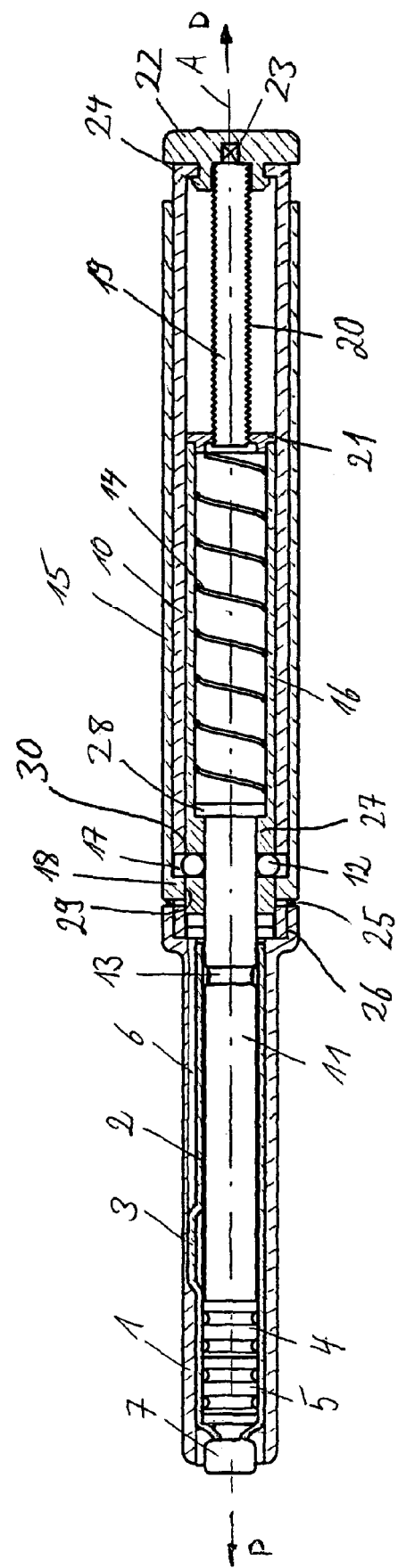
FIG. 3 is a sectional representation of the injection device of FIGS. 1 and 2, at the end of the delivery process.

The injection pen shown in FIG. 1 comprises a front casing part 1 and a rear casing part 10 which are screwed together by means of co-operating threads 26. The front casing part 1 contains a two-chamber ampoule 2. The two-chamber ampoule 2 comprises a bypass 3 on its wall and a facing surface with a closure 7 at its front end facing in the distal direction P. A closing piston 4 and a dividing piston 5 are located in the two-chamber ampoule 2 and are both located in a proximal arrangement with respect to the bypass 3. The two pistons 4, 5 abut the inner wall of the two-chamber ampoule 2, outside the bypass 3, forming a seal. A fluid product 8 is located in the space between the closing piston 4 and the dividing piston 5. A dry, mostly powdery substance 9, which together with the fluid product 8 forms a mixed product 8, 9, is located in the space between the closure 7 and the dividing piston 5. The two-chamber ampoule 2 is introduced into the front casing part 1 via its proximal end, to which end a groove 6 running in an axial direction A is contained in the front casing part 1 and creates a space for the bypass 3 of the two-chamber ampoule 2.

The rear casing part 10 substantially contains the piston rod 11, spheres 12 acting as holding elements, a retainer 16, a threaded nut 21, a threaded rod 19 and a coil spring 14. A rotating knob 22 is attached to the proximal end of the injection device and is connected to the threaded rod 19 by two elements 23 co-operating in a positive lock. Locking elements 24 formed on the rotating knob 22 grip behind a collar which faces radially inwards and is formed on the proximal end of the rear casing part 10, such that the rotating knob 22 cannot be moved axially relative to the rear casing part 10, but exhibits a rotational degree of freedom. A threaded drive 19/21 is formed by the threaded nut 21 via the outer thread 20 attached to the threaded rod 19. The threaded nut 21 is rotationally fixed in the rear casing part 10, but can be moved axially. The threaded nut 21 is connected to a retainer 16 which can also only be moved in the axial direction A in the rear casing part 10. The threaded nut 21 and the retainer 16 are fixedly connected to each other, such that it is only necessary to rotationally fix one of the two components 16, 21 in order to obtain a rotational block. A radial heel 27 is attached to the distal end of the retainer 16 and simultaneously serves as an axial guide for the piston rod 11. Guides 30 which run in an approximately radial direction are attached in the area of the radial heel 27 for each of the spheres 12 serving as a holding element. These guides 30 are preferably bores having a circular cross-section and thus corresponding to the cross-section of the spheres 12. An annularly circumferential groove 13, with which the spheres 12 engage, is located on the piston rod 11 and approximately exhibits the contour of the spheres 12.

The outer casing part 10 guides the retainer 16 axially and simultaneously forms a radial stopper for the spheres 12, such that they cannot be pressed out of the groove 13. A radial collar 28 is located at the proximal end of the piston rod 11 and is also guided by the peripheral surface of the retainer 16. Before a delivery process, there is a distance d1 between the radial collar 28 and the radial heel 27. The coil spring 14 surrounding the threaded rod 19 is located between the radial collar 28 and the threaded nut 21. The coil spring 14 is biased and exerts a force in the distal direction on the piston rod 11. Initially, however, the coil spring 14 cannot move the piston rod 11 axially, since the piston rod 11 is blocked by the spheres 12.

The blending process and/or blending movement is caused by rotating the rotating knob 22. The rotation transferred onto the threaded rod 19 is converted via the thread pitch and via the rotationally fixed threaded nut 21 into an axial movement which is transferred via the retainer 16 and the holding elements and/or spheres 12 onto the piston rod 11. The retainer 16, the piston rod 11, the spheres 12, the threaded nut 21 and the coil spring 14 are thus moved towards the distal end of the injection device, without the coil spring 14 being relaxed. The distance d2, formed by facing sides of the proximal end of the front casing part 1 and the retainer 16, decreases with the number of rotations of the rotating knob 22.

Moving the piston rod 11 in the distal direction P shifts the closing piston 4 in the distal direction P in the two-chamber ampoule 2. Due to the incompressibility of the fluid product 8, the dividing piston 5 is likewise moved in the distal direction P until it has completely reached the area of the bypass 3. Since the dividing piston 5 then no longer forms a seal, the fluid product 8 can flow via the bypass 3 past the dividing piston 5 into the front chamber of the two-chamber ampoule 2 and thus mix with the product 9. The blending process is complete when the closing piston 4 abuts the dividing piston 5 and has thus displaced almost the entire fluid product 8 between them.

At the end of the blending process, the spheres 12 are simultaneously located axially in the area of blocking elements 18 connected to a triggering sleeve 15 which at least partially encloses the rear casing part 10. The surfaces 29 of the blocking elements 18, facing radially with respect to the longitudinal axis A, have approximately the same radial distance from the longitudinal axis A as the inner wall of the rear casing part 10. In this way, the surfaces 29 still press the spheres 12 into the groove 13 of the piston rod 11.

The administering process is triggered by the axial movement of the triggering sleeve 15 in the distal direction P. The windows 17 contained in the rear casing part 10 allow the axial movement of the triggering sleeve 15. The axial force which is exerted by the coil spring 14 on the piston rod 11 presses the spheres 12 radially outwards into the windows 17, since the groove 13 is shaped such that, due to the axial force on the piston rod 11, at least a force component acting radially outwards acts on the spheres 12. Once the spheres 12 have entered the windows 17, the piston rod 11 is released, such that it is moved by the biased coil spring 14 relative to the retainer 16 in the distal direction P. The piston rod 11 then presses the two pistons 4, 5 in the distal direction P and thus delivers the mixed product 8, 9. If, at the start of the delivery process, the distance from the dividing piston 5 to the distal facing surface of the two-chamber ampoule 2 is larger than the distance d1, the piston rod 11 merely travels the path d1 within the scope of the delivery movement. If the distance between the dividing piston 5 and the distal facing side of the two-chamber ampoule 2 is smaller than the distance d1, then the mixed product 8, 9 is completely delivered from the two-chamber ampoule 2 without the path d1 having been completely traveled.

During the delivery process, the spheres 12 are located in the windows 17, wherein the triggering sleeve 15 prevents the spheres 12 from falling out of the windows 17. At this time, the triggering sleeve 15 cannot be moved back to its original position, since the spheres 12 remain pressed into the windows 17 by the peripheral surface of the piston rod 11.

In order to blend and administer the products of a two-chamber ampoule 2 again, the injection device has to be returned to its original position. To this end, the piston rod 11 is pressed in the proximal direction D. As soon as the groove 13 reaches the axial area of the spheres 12, the spheres 12 are pressed back into the groove 13 due to the spring 25 which exerts an axial force on the triggering sleeve 15 and thus exerts at least a portion of the force, facing radially with respect to the longitudinal axis A, on each of the spheres 12. The triggering sleeve 15 is snapped back into its original position by the blocking elements 18 due to the elasticity force of the spring 25. The surfaces 29 then again hold the spheres 12 firmly in the groove 13, such that the piston rod 11 is prevented from moving axially relative to the retainer 16.

The mechanism, consisting of the retainer 16, the piston rod 11, the spheres 12, the threaded nut 21 and the coil spring 14, is moved back to its original position by rotating the rotating knob 22 back in a rotating direction counter to the blending movement. The front casing part 1 can then be fitted with a new two-chamber ampoule 2 and screwed onto the rear casing part 10 by the thread connection 26. The injection device is then once again ready for a new blending/delivery of the products in/from the two-chamber ampoule 2.

Embodiments of the present invention, including preferred embodiments, have been presented for the purpose of illustration and description. They are not intended to be exhaustive or to limit the invention to the precise forms or steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device for use with a two-chamber ampoule, comprising:
   a front casing part with which the two-chamber ampoule can be associated;
   a rear casing part coupled to the front casing part;
   a retainer positioned within the rear casing part and axially slidable relative to the rear casing part;
   a threaded rod to which the retainer is rotatably coupled such that rotation of the threaded rod moves the retainer axially in a dispensing direction, wherein the threaded rod is not axially movable relative to the rear casing;
   a piston rod and an associated piston arranged proximate a distal end of the piston rod;
   a spring operably coupled between the retainer and a proximal end of the piston rod;
   wherein the threaded rod is rotated to move the retainer, spring and piston rod in the dispensing direction, whereby the piston rod moves the piston in the dispensing direction until blending is achieved, creating a blended dose;
   wherein dispensing of the blended dose is performed by releasing the spring to drive the piston rod and piston in the dispensing direction;
   wherein the spring is biased and the piston rod is released when at least one holding element is released;
   wherein the at least one holding element engages with a groove in the piston rod and is fixed relative to the piston rod during the blending movement;
   wherein the at least one holding element is pressed into the groove in the piston rod by a blocking element at a position of the piston rod which is reached at the end of the blending movement; and
   wherein the blocking element protrudes through a window introduced in the rear casing part.

2. The injection device according to claim 1, wherein the piston rod carries out an axial movement relative to a threaded nut associated with the threaded rod during the delivery movement.

3. The injection device according to claim 2, wherein the piston rod is axially fixed relative to the threaded nut during the blending movement.

4. The injection device according to claim 1, wherein the at least one holding element is pressed into the groove by the rear casing part during the blending movement, and in that the at least one holding element is thus moved relatively along the rear casing part.

5. The injection device according to claim 1, wherein the at least one blocking element releases the at least one holding element by a translational or a rotational movement, such that each of them is pressed approximately radially outwards due to a force acting on the at least one holding element.

6. The injection device according to claim 1, wherein during a delivery process, the at least one holding element is pressed into the window of the rear casing part, against a triggering sleeve slid over it.

7. The injection device according to claim 6, wherein an elastic element moves the triggering sleeve back to the position which the triggering sleeve had before the at least one holding element was released.

8. The injection device according to claim 1, wherein an axial position of the at least one holding element relative to a threaded nut of the threaded drive is kept constant by the retainer.

9. The injection device according to claim 1, wherein the at least one holding element is at least one sphere.

10. The injection device according to claim 9, wherein the groove exhibits a depth corresponding at most to a radius of the at least one sphere, such that when an axial force is exerted on the piston rod, at least a force component acts radially outwards on the at least one sphere.

11. The injection device according to any one of claim 9, wherein the groove exhibits a width which is smaller than a diameter of the at least one sphere, such that when an axial force is exerted on the piston rod, at least a force component acts radially outwards on the at least one sphere.

12. The injection device according to claim 1, wherein the at least one blocking element releases the at least one holding element by a translational or a rotational movement, such that the at least one holding element is pressed approximately radially outwards due to a force acting on the at least one holding element.

13. An injection device for use with a two-chamber ampoule, comprising:
   a front casing part with which the two-chamber ampoule can be associated;
   a rear casing part coupled to the front casing part;
   a retainer positioned within the rear casing part and axially slidable relative to the rear casing part;
   a threaded rod to which the retainer is rotatably coupled such that rotation of the threaded rod moves the retainer axially in a dispensing direction, wherein the threaded rod is not axially movable relative to the rear casing;
   a piston rod and an associated piston arranged proximate a distal end of the piston rod;
   a spring operably coupled between the retainer and a proximal end of the piston rod;
   wherein the threaded rod is rotated to move the retainer, spring and piston rod in the dispensing direction, whereby the piston rod moves the piston in the dispensing direction until blending is achieved, creating a blended dose;
   wherein dispensing of the blended dose is performed by releasing the spring to drive the piston rod and piston in the dispensing direction;

wherein the spring is biased and the piston rod is released when at least one holding element is released;

wherein the at least one holding element engages with a groove in the piston rod and is fixed relative to the piston rod during the blending movement;

wherein the at least one holding element is pressed into the groove in the piston rod by a blocking element at a position of the piston rod which is reached at the end of the blending movement; and wherein the blocking element is affixed to a triggering sleeve which at least partially encloses the rear casing part.

14. The injection device according to claim 13, wherein the piston rod carries out an axial movement relative to a threaded nut associated with the threaded rod during the delivery movement.

15. The injection device according to claim 14, wherein the piston rod is axially fixed relative to the threaded nut during the blending movement.

16. The injection device according to claim 13, wherein the at least one holding element is pressed into the groove by the rear casing part during the blending movement, and in that the at least one holding element is thus moved relatively along the rear casing part.

17. The injection device according to claim 13, wherein the at least one blocking element releases the at least one holding element by a translational or a rotational movement, such that each of them is pressed approximately radially outwards due to a force acting on the at least one holding element.

18. The injection device according to claim 13, wherein the blocking element protrudes through a window introduced in the rear casing part.

19. The injection device according to claim 18, wherein during a delivery process, the at least one holding element is pressed into the window of the rear casing part, against the triggering sleeve slid over it.

20. The injection device according to claim 19, wherein an elastic element moves the triggering sleeve back to the position which the triggering sleeve had before the at least one holding element was released.

21. The injection device according to claim 13, wherein an axial position of the at least one holding element relative to a threaded nut of the threaded drive is kept constant by the retainer.

22. The injection device according to claim 13, wherein the at least one holding element is at least one sphere.

23. The injection device according to claim 22, wherein the groove exhibits a depth corresponding at most to a radius of the at least one sphere, such that when an axial force is exerted on the piston rod, at least a force component acts radially outwards on the at least one sphere.

24. The injection device according to any one of claim 22, wherein the groove exhibits a width which is smaller than a diameter of the at least one sphere, such that when an axial force is exerted on the piston rod, at least a force component acts radially outwards on the at least one sphere.

25. The injection device according to claim 13, wherein the at least one blocking element releases the at least one holding element by a translational or a rotational movement, such that the at least one holding element is pressed approximately radially outwards due to a force acting on the at least one holding element.

* * * * *